(12) United States Patent
Isago et al.

(10) Patent No.: US 8,524,890 B2
(45) Date of Patent: Sep. 3, 2013

(54) WATER-SOLUBLE PHTHALOCYANINE DYE

(75) Inventors: Hiroaki Isago, Tsukuba (JP); Yutaka Kagaya, Tsubuka (JP); Youichi Oyama, Tsukuba (JP); Harumi Fujita, Tsukuba (JP)

(73) Assignee: National Institute for Materials Science, Tsukuba-Shi (JP)

( * ) Notice: Subject to any disclaimer, the term of this patent is extended or adjusted under 35 U.S.C. 154(b) by 162 days.

(21) Appl. No.: 13/138,426

(22) PCT Filed: Feb. 24, 2010

(86) PCT No.: PCT/JP2010/052884
§ 371 (c)(1),
(2), (4) Date: Aug. 12, 2011

(87) PCT Pub. No.: WO2010/098359
PCT Pub. Date: Sep. 2, 2010

(65) Prior Publication Data
US 2011/0301344 A1    Dec. 8, 2011

(30) Foreign Application Priority Data
Feb. 24, 2009 (JP) .................. 2009-040073

(51) Int. Cl.
*C09B 47/04* (2006.01)

(52) U.S. Cl.
USPC ........................................ 540/140

(58) Field of Classification Search
USPC ........................................ 540/140
See application file for complete search history.

(56) References Cited

FOREIGN PATENT DOCUMENTS
JP    2005-060575    3/2005

OTHER PUBLICATIONS

Synthesis of Phthalocyanines-ALA Conjugates: Water-Soluble compounds with Low Aggregation; Received Aug. 4, 2009; American Chemical Society.

*Primary Examiner* — Brian McDowell
(74) *Attorney, Agent, or Firm* — Manabu Kanesaka

(57) ABSTRACT

The invention has for its object to provide a water-soluble phthalocyanine dye unlikely to lose its own properties even upon dissolved in a concentration as high as $10^{-5}$ M.
The inventive water-soluble phthalocyanine dye is characterized by having a sulfuric acid group or groups as an axial ligand or ligands of an antimony/phthalocyanine complex. The sulfuric acid group or groups have been introduced by replacing a part or the whole of hydroxyl groups in the starting material with a sulfuric acid group or groups.

1 Claim, 7 Drawing Sheets

WATER-SOLUBLE PHTHALOCYANINE DYE

RELATED APPLICATIONS

The present application is National Phase of International Application No. PCT/JP2010/052884 filed Feb. 24, 2010, and claims priority from, Japanese Application No. 2009-040073 filed Feb. 24, 2009, the disclosure of which is hereby incorporated by reference herein in its entirety.

BACKGROUND OF THE INVENTION

1. Field of the Art

The present invention relates to a phthalocyanine dye that is soluble in water.

2. Description of the Prior Art

Phthalocyanine and its metal complexes (FIG. 1) are organic dyes having a large π conjugate system.

However, those dyes have a planar feature high enough to cause interactions to take place between dye molecules, making it poorly soluble not only in water but in general organic solvents as well.

To solve this problem, many attempts have so far been made, which includes an attempt wherein the hydrogen atoms in benzene rings on the outer side of phthalo-cyanine are substituted by other side-chain groups or an axial ligand is coordinated in a phthalocyanine complex to make solubility in general organic solvents much higher, as reported in Non-Patent Publications 1 to 5 and Patent Publication 1. However, nearly all of them were unsuccessful in improvements in their water solubility.

Specifically, Non-Patent Publication 1 has reported a phthalocyanine dye that forms hydrophilic colloid, but that colloid is far away from being soluble in water.

In Non-Patent Publication 2, the hydrogen atoms in the benzene rings are substituted by hydrophilic functional groups such as sulfonic acid groups ($-SO_3H$) to introduce some improvements in solubility in water, but significant molecular aggregation occurs in an aqueous solution.

In Non-Patent Publications 3, 4 and 5, the hydrogen atoms in the benzene ring are substituted by hydrophilic functional groups such as carboxyl groups ($-CO_2H$) to introduce some improvements in solubility in water, but significant molecular aggregation occurs in an aqueous solution.

In most of the prior arts, the hydrogen atoms in the benzene rings are substituted by hydrophilic functional groups such as sulfonic acid groups ($-SO_3H$) or carboxyl groups ($-CO_2H$) or their analogs to improve solubility in water. However, it has been known that the phthalo-cyanine that is made water soluble in this way causes significant molecular aggregation (that is a phenomenon in which multiple molecules behave as if they were one single molecule) at high concentrations, giving rise to losses of the characteristic features inherent in the phthalocyanine dye (photochemical feature in particular).

In Patent Publication 1, axial ligands X and Y derived from an oxidizing agent are used as the groups capable of being coordinated at the antimony of an antimony/phthalocyanine complex; however, that publication refers only to halogens, organic peroxides, peracids or acid halides, saying nothing about the selection of a specific axial ligand for improving water solubility.

LISTING OF THE PATENT PUBLICATIONS

Patent Publication 1: U.S. Pat. No. 4,038,572

LISTING OF THE NON-PATENT PUBLICATIONS

Non-Patent Publication 1: Journal of Inorganic Biochemistry., 102 (2008)380, H. Isago, K. Miura, Y. Oyama (issued on Mar. 6, 2008)
Non-Patent Publication 2: Inorg. Chem., 4 (1965)469, J. H. Weber and D. H. Bush
Non-Patent Publication 3: Makromol. Chem., 181(980)2127, 2127, D. Wohrle and G. Meyer
Non-Patent Publication 4: Makromol. Chem., 181 (1980) 575, H. Shirai et al.
Non-Patent Publication 5: Phthalocyanines: Properties and Applications, 1989 VCH Publishers, Inc., C. C. Leznoff

SUMMARY OF THE INVENTION

Object of the Invention

With such situations in mind, the present invention has for its object the provision of a water-soluble phthalocyanine dye unlikely to lose its own properties even upon being dissolved in a concentration as high as $10^{-5}$ M.

Means for Accomplishing the Object

According to the first aspect of the invention, the water-soluble phthalocyanine dye is characterized by having a sulfuric acid group or groups as an axial ligand or ligands of an antimony/phthalocyanine complex.

According to the second aspect of the invention, the water-soluble phthalocyanine dye of the first aspect is further characterized in that said axial sulfuric acid group or groups have been introduced by replacing a part or the whole of hydroxyl groups in the starting material with a sulfuric acid group or groups.

Advantages of the Invention

It has now been found that the axial ligand of an antimony/phthalocyanine complex governs water solubility, and has some significant relation to the maintenance of its own properties. Such findings underlie the inventions according to both aspects.

As a result, the inventive phthalocyanine dye does not aggregate even at relatively high concentrations (>$10^{-5}$ M) and presents as a monomer, and keeps its own features intact.

EMBODIMENTS FOR CARRYING OUT THE INVENTION

1. The Number of the Sulfuric Group that is the Axial Ligand: One or Two

Although the example, given later, refers only to two hydroxyl groups, yet the same advantage would be expected to be obtained even with one hydroxyl group. Dyes comprising one sulfuric acid group and one hydroxyl group may be obtained by under different synthetic conditions too, and would be considered to have the same functions as in the example given below. In mass analysis, too, such chemical species have been detected under different ionizing conditions.

2. Dissociation of the Sulfuric Acid Group or Groups

Figure 4A:
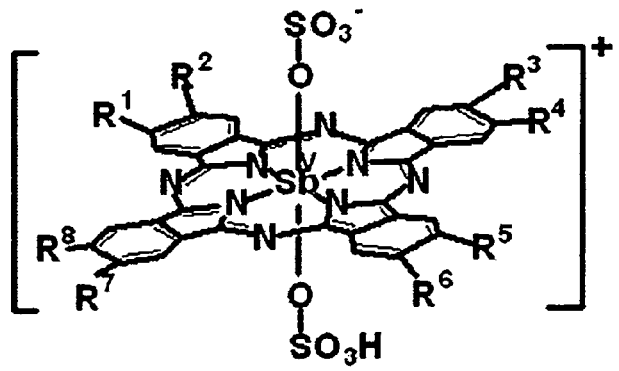
FIG. 4 is a chemical formula of a water-soluble phthalocyanine obtained in the inventive example.

The dye isolated as a solid in the instant example would be considered to be a neutral species (twitter ions) having such a structure as shown in FIG. 4a. As will be described with reference to FIG. 4, however, there are cationic species and anionic species occurring because of acid dissolution equilibrium of the sulfuric acid group or groups; in other words, it is nonsense to make discriminations between the chemical species (FIGS. 4a to 4c) stemming from the acid dissociation of the sulfuric acid group or groups.

3. Types of Peripheral Substituents ($R^{1-8}$ in FIG. 3)

Given in the instant embodiment are an example with no peripheral substituent, an example using a tert-butyl group as the hydrocarbon group, and an example using an n-butoxy group as the heteroatom-containing hydrocarbon group. It is here to be noted that the latter two are introduced chiefly for the purpose of improving the solubility of the phthalocyanine dye in solvents, making no or little contribution to its solubility in water in particular. Apart from a functional group like an amino group capable of reaction with sulfuric acid, therefore, the same advantages as in the example, given below, would be obtained even with other substituents while allowing them to function on their own.

Furthermore, phthalocyanine dyes having only electron withdrawing substituents such as halogens, nitro groups and cyano groups have much lower solubility in solvents. However, it has been ascertained by the example, given below, that even unsubstituted dyes ($R^{1, 3, 5, 7} = R^{2, 4, 6, 8} = H$) having similar lower solubility can be dissolved in an aqueous solution, so there is no reason to exclude them. Therefore, if pentavalent antimony and the axial sulfuric acid group coexist, the same advantages as in the example, given below, would be obtained even with phthalocyanine dyes having any peripheral substituents known so far in the art (unless that they react with sulfuric acid). The pentavalent antimony-containing phthalocyanine dye (FIG. 3) used in the example, given below, was synthesized by the process set forth in Patent Publication 1 (the inventors: Hiroaki ISAGO and Yutaka KAGAYA). Especially, dyes having a tert-butyl group as the peripheral substituent are described in detail in Non-Patent Publication 1.

A dye having no peripheral substituent and the dye (FIG. 3) having n-butoxy groups as the peripheral substituent were respectively synthesized by the oxidization with t-butyl perbenzoate of a phthalocyanine compound of trivalent antimony synthesized by heating a mixture of phthalonitrile having a corresponding substituent and antimony iodide.

It should be noted that although not described in the following example, there could be the possibility of oxidizing trivalent Sb complexes with, for instance, persulfuric acid into pentavalent complexes having a sulfuric acid group or groups.

EXAMPLE

Set out below is an example of how to prepare the inventive water-soluble phthalocyanine dyes.

Figure 1:
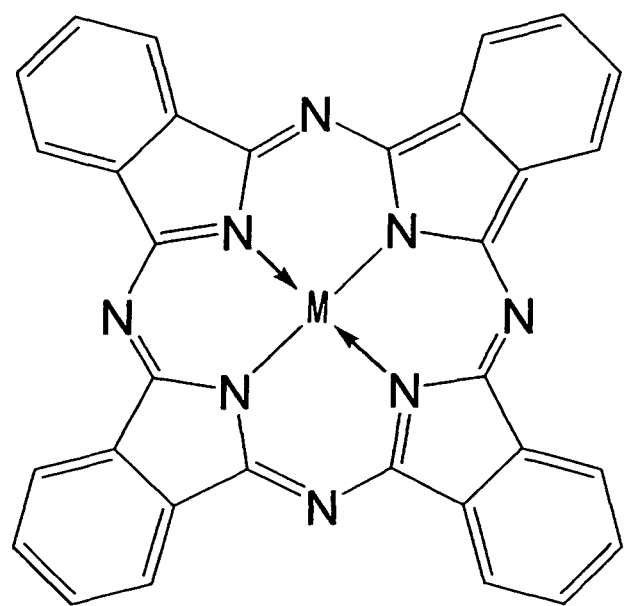
FIG. 1 is a chemical formula indicative of a metal complex of phthalocyanine.
Figure 2:
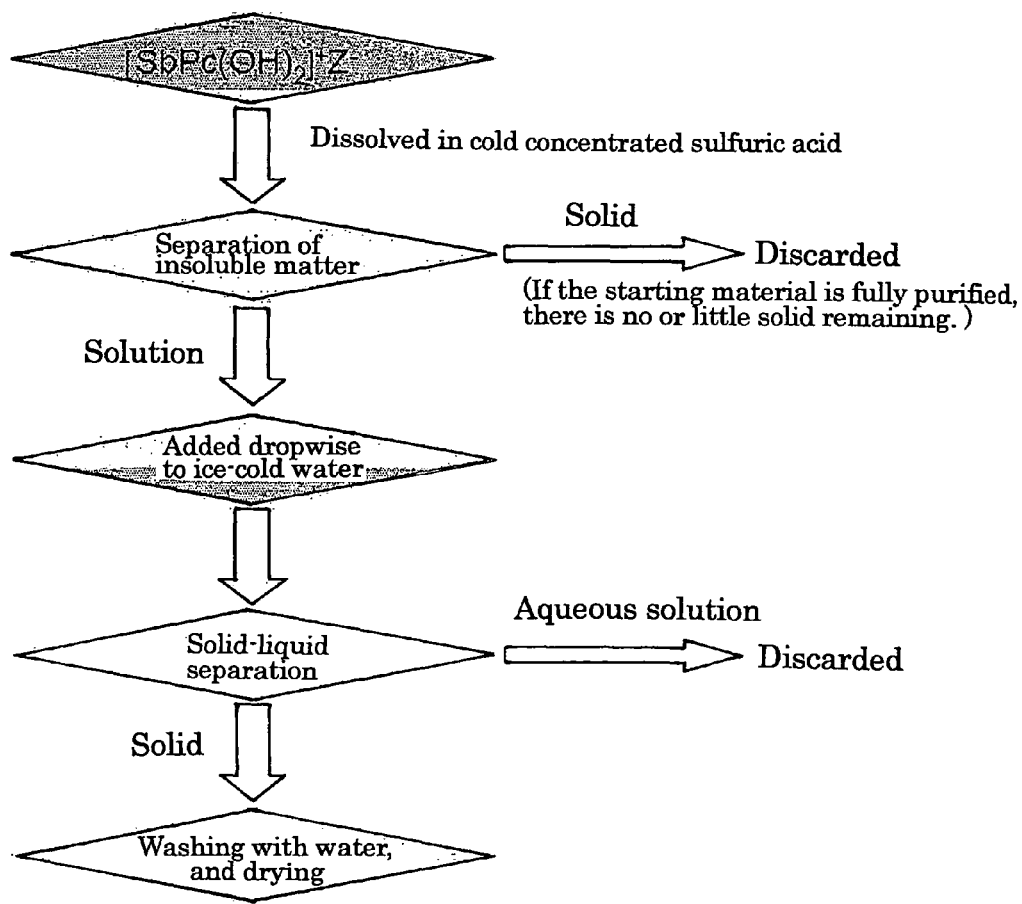
FIG. 2 is a synthetic flowchart for the inventive water-soluble phthalocyanine dye.
Figure 3:
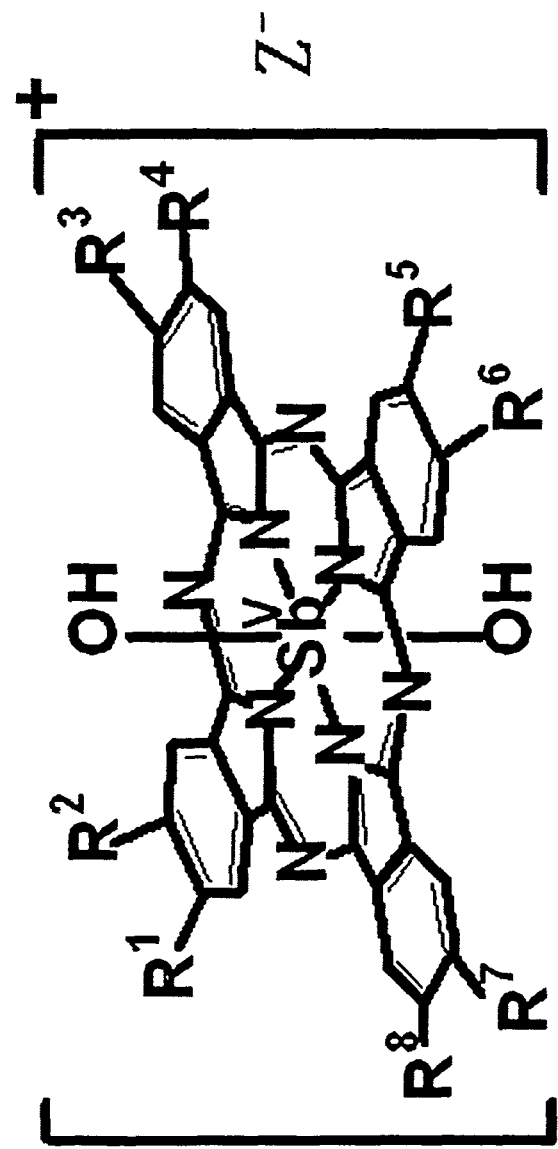
FIG. 3 is a chemical formula indicative of a phthalocyanine complex of pentavalent antimony used as the starting material in the inventive example.

The starting phthalocyanine dye, which is represented in a formula $[SbPc(OH)_2]^+Z^-$ in FIG. 2, has such a structure as shown in FIG. 3 that will be explained in detail. This starting material is dissolved in a minimum amount of concentrated sulfuric acid necessary to dissolve it, then the solution is filtered, and then the filtrate is added dropwise to ice-cold water where the dye is liberated as a solid. The solid is collected by filtration, and then dried after washed with cold water (until the washing water becomes neutral). Whenever necessary, the solid may be recrystallized from an appropriate organic solvent system. An example of using the tert-butyl group as the peripheral substituent is now explained (Compound 2 in Table 1).

One hundred (100) mg of $[Sb(tbpc)(OH)_2]^+I_3^-$ (tbpc=tetra-t-butyl substituted phthalocyanine; 0.077 mmol) are dissolved in 3 ml of ice-cold concentrated sulfuric acid, and filtered to remove a trace amount of insoluble matter, after which the filtrate is added dropwise to about 100 g of ice. The obtained blue greenish solid is washed with water until the washing water becomes almost neutral (pH 5 to 6), and dried at 60° C. for a whole day and night.

This solid is dissolved in 3 ml of ethanol, and filtered to remove a trace amount of insoluble matter, after which 30 ml of hexane are added to precipitate the solid. Subsequently, the solid is dissolved in 1 ml of dichloromethane, and 8 ml of hexane are added to the solution for precipitation of the solid that is then collected by centrifugation, and vacuum dried at 80° C. for 12 hours to obtain the desired solid in an amount of 47 mg (0.041 mmol) (in 53% yields).

As a result of elemental analysis, the obtained solid has been found to have 50.54% (w/w) of carbon, 4.93% (w/w) of hydrogen and 9.99% (w/w) of nitrogen, of which the values are close to the theoretical value (50.49% (w/w) of carbon, 5.21% (w/w) of hydrogen and 9.81% (w/w) of nitrogen) for $[Sb(tbpc)(SO_4)(HSO_4)] \cdot 4H_2O(C_{48}H_{57}N_8O_{12}S_2Sb)]$.

The water-soluble dye having no peripheral substituent (Compound 1 in Table 1) and the water-soluble dye having the n-butoxy groups (Compound 3 in Table 1) were likewise synthesized by adding a solution dropwise to ice, in which solution the starting dye (FIG. 3) having the corresponding peripheral substituents was dissolved in ice-cold concentrated sulfuric acid, and then was treated in a similar way to that for Compound 2.

FIG. 3 is illustrative of the structure of the phthalocyanine dye used as the staring material in the instant example, in which pentavalent antimony is used as the central element of the phthalocyanine dye. In addition, the axial hydroxyl groups (OH groups) is used as inlets for the hydrophilic functional groups for making the dye soluble in water. In FIG. 3, the $R^1$ to $R^8$ are side-chain groups called the peripheral substituents that play a role of increasing the solubility of phthalocyanine dye, which is generally poorly soluble in common solvents. As shown in the instant example (Table 1), therefore, hydrocarbons and heteroatom (such as oxygen and sulfur)-containing hydrocarbons are used. The substituents $R^1$ to $R^8$ may be identical to or different from one another, and a part of them may merely be a hydrogen atom or atoms. All of them may be hydrogen atoms as exemplified in the instant example, although its solubility may be poor.

The $Z^-$ on the right side of FIG. 3 stands for a counter anion. The pentavalent antimony-containing phthalocyanine dye is charged to +1 all over the molecule, and the charges must be neutralized by the counter anion $Z^-$. In the example, $Z^-$ is exemplified by $I_3^-$ for the simple reason that the starting material is easily available in the form of $I_3^-$ salt. Whenever necessary, it may be converted through ion exchange into other salts (for instance, $BF_4^-$, $PF_6^-$, and $ClO_4^-$).

In the process of dissolving the starting material in concentrated sulfuric acid and then treating the solution with cold water, however, there is a great likelihood that the counter ions may be lost and converted into a salt of other anions. In the example, indeed, it has been confirmed by optical absorption spectra that $I_3^-$ that is the anion in the starting material has been lost. In other words, there is no need of taking the trouble to convert it into other salt: this is the reason that $I_3^-$ was not turned into other salt in the instant example.

Figure 4B:
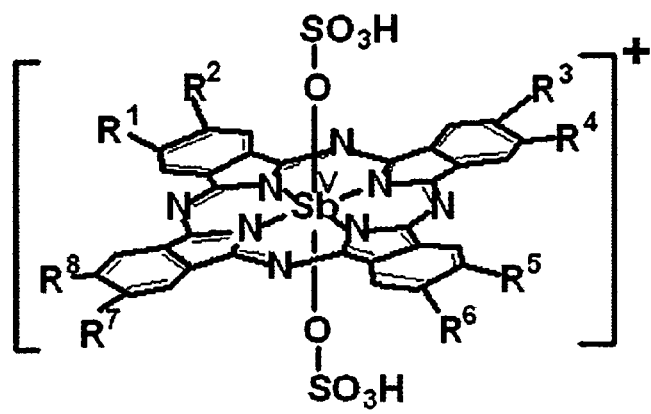
Figure 4C:
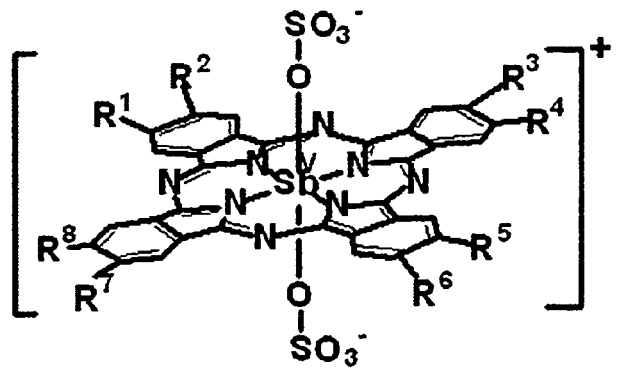

FIG. 4a is indicative of the structure of the water-soluble phthalocyanine dye obtained by the synthetic process of FIG. 2. As in FIG. 3, the central element of the phthalocyanine dye is pentavalent antimony, and $R^1$ to $R^8$ are the same peripheral substituents as those in FIG. 3. Only the axial ligands have been changed from the hydroxyl groups (—OH groups) to the sulfuric acid groups (—$OSO_3H$ or —$OSO_3$—). The structure of FIG. 4a shows an electrically neutral species. Unless either of the two sulfuric acid groups are deporotonated, there will be a cationic species occurring (FIG. 4b). If both are dissociated, on the contrary, there will be an anionic species occurring (FIG. 4c). That is, there would be an equilibrium mixture of three chemical species in the solution. When isolated as a solid, the phthalocyanine dye must be electrically neutral. On the other hand, the possibility of the presence of $I_3^-$ as the counter ion, which is from the starting material, is excluded based on the optical absorption spectra. In addition, the prospected anions were not detected in mass spectra (negative scan mode). All these would indicate that the cationic species detected in the mass spectrum (FIG. 5) has no counter ion, and hence one of the axial sulfuric acid groups is subjected to acid dissociation (into —$OSO_3^-$) to neutralize the positive and negative charges within the molecule (the so-called twitter ion state).

Figure 5:
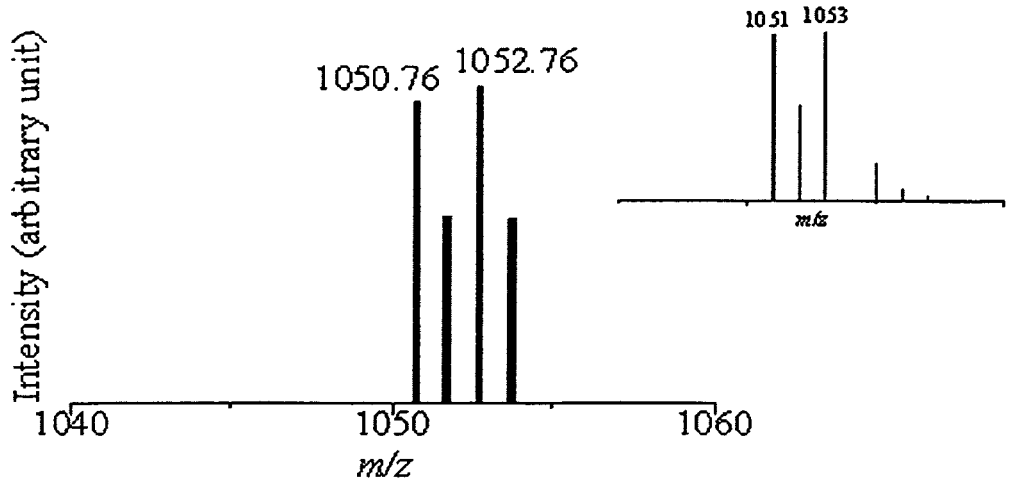
FIG. 5 is a graph indicative of the mass spectra (acetone solution) of Compound 2 in Table 1 and the theoretical spectra of Compound 2 based on an isotope abundance.

FIG. 5 is one exemplary mass spectra (ESI-MS) of the water-soluble phthalocyanine dye of FIG. 4 as measured in an acetone solution, and stands for spectra in the case where the peripheral substituents are $R^{1,3,5,7}$=H, $R^{2,4,6,8}$=tert-butyl group (—$C(CH_3)_3$): Compound 2). FIG. 5 also shows the theoretical spectra figured out on the basis of a natural isotope abundance and on the presumption of the cation species (FIG. 4b) where both sulfuric acid groups are not dissociated in the molecular structure of FIG. 4. Both spectra match very well. As explained with reference to FIG. 4, there is an equilibrium mixture of three chemical species including this cationic species in the solution, and the measurement is carried out in the positive scan mode; the experimental results are not contradictory to FIG. 4a. A reason for the appearance of a pair of strong peaks being detected at molecular weights of about 1,051 and about 1,053 is that antimony has two stable isotopes ($^{121}Sb$ and $^{123}Sb$) present in nearly the same ratio. Although depending on measuring conditions, the axial ligands may be detected as a sodium salt (i.e., —$OSO_3Na$) or a potassium salt (—$OSO_3K$) or a mixture of both but not as a protonated sulfuric acid group (—$OSO_3H$). Anions (for instance, $I_3^-$ and $SO_4^{2-}$ contained in the starting material) were not detected by negative scan measurement (in the mode of detecting anions), either.

Figure 6:
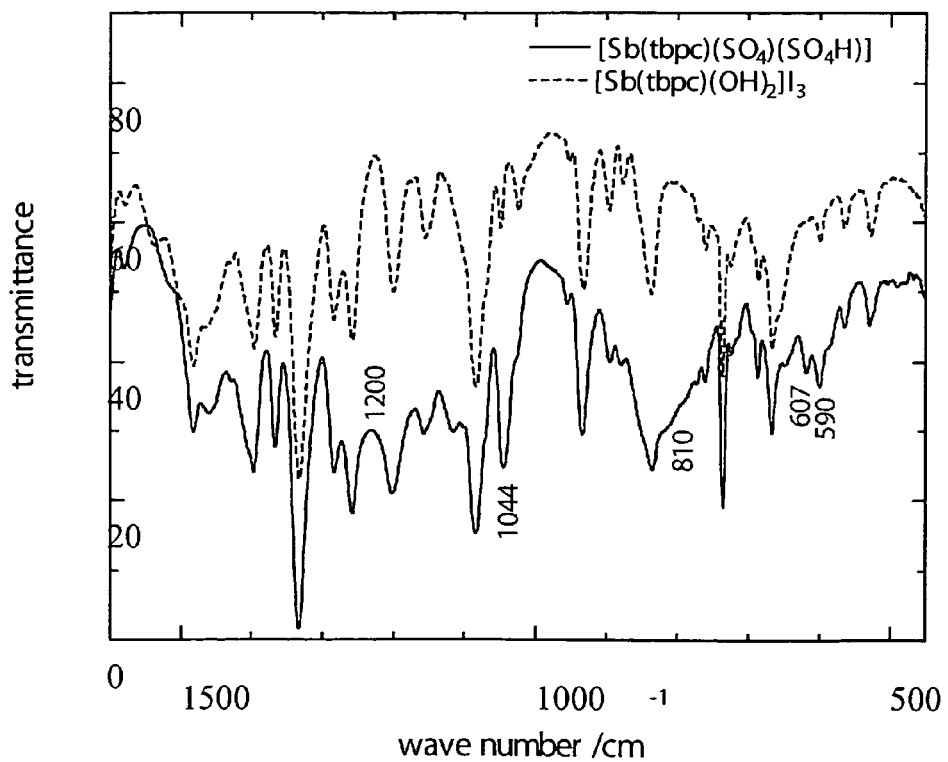
FIG. 6 is a graph indicative of the IR spectra of Compound 2 in Table 1.

FIG. 6 (solid line) shows an exemplary IR spectra (KBr diffuse reflection method) of the water-soluble phthalocyanine dye (Compound 2; $R^{1,3,5,7}$=H and $R^{2,4,6,8}$=tert-butyl group (—$C(CH_3)_3$) in FIG. 4. The spectrum exhibits a pair of sharp absorption bands at 590 $cm^{-1}$ and 607 $cm^{-1}$, a broad absorption band at 800 $cm^{-1}$ to 900 $cm^{-1}$, and a strong absorption band at 1,044 $cm^{-1}$, which are not observed in the spectra (broken line) of the starting dye. The former two are ascribed to the bending vibration of the sulfuric acid group coordinated to the metal ion, while the latter two are ascribed to the stretching vibration of S—O, making sure the bond of Sb—$OSO_3^-$ exists.

Figure 8:
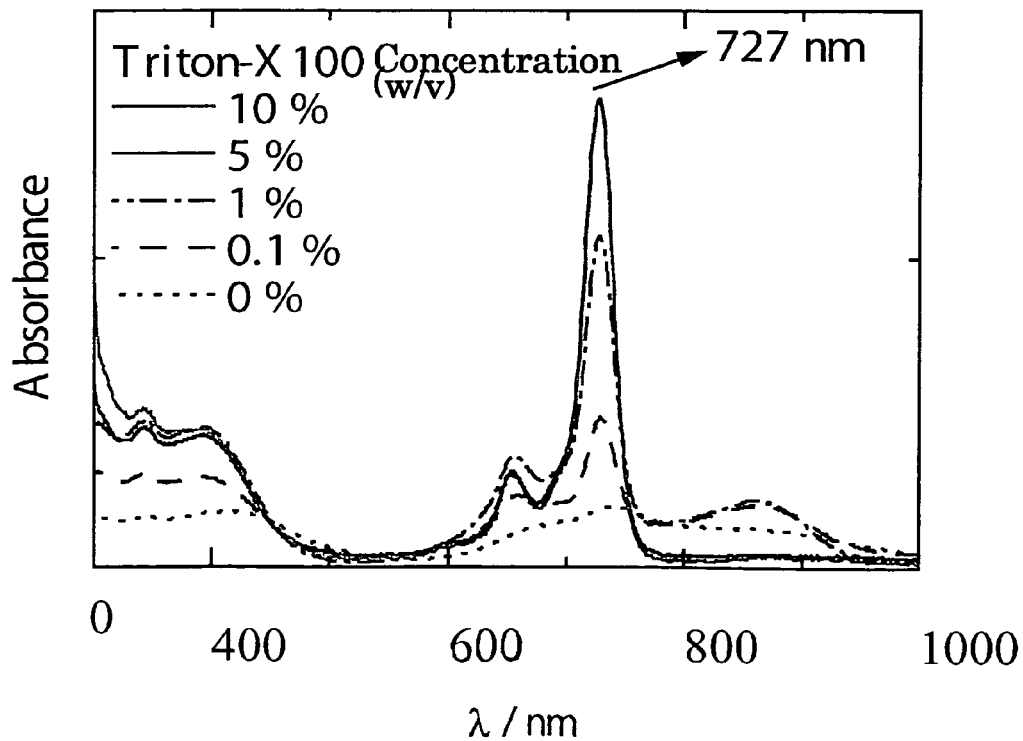
FIG. 8 is a graph indicative of the optical absorption spectra (aqueous solution) of Compound 2 in Table 1.
Figure 9:
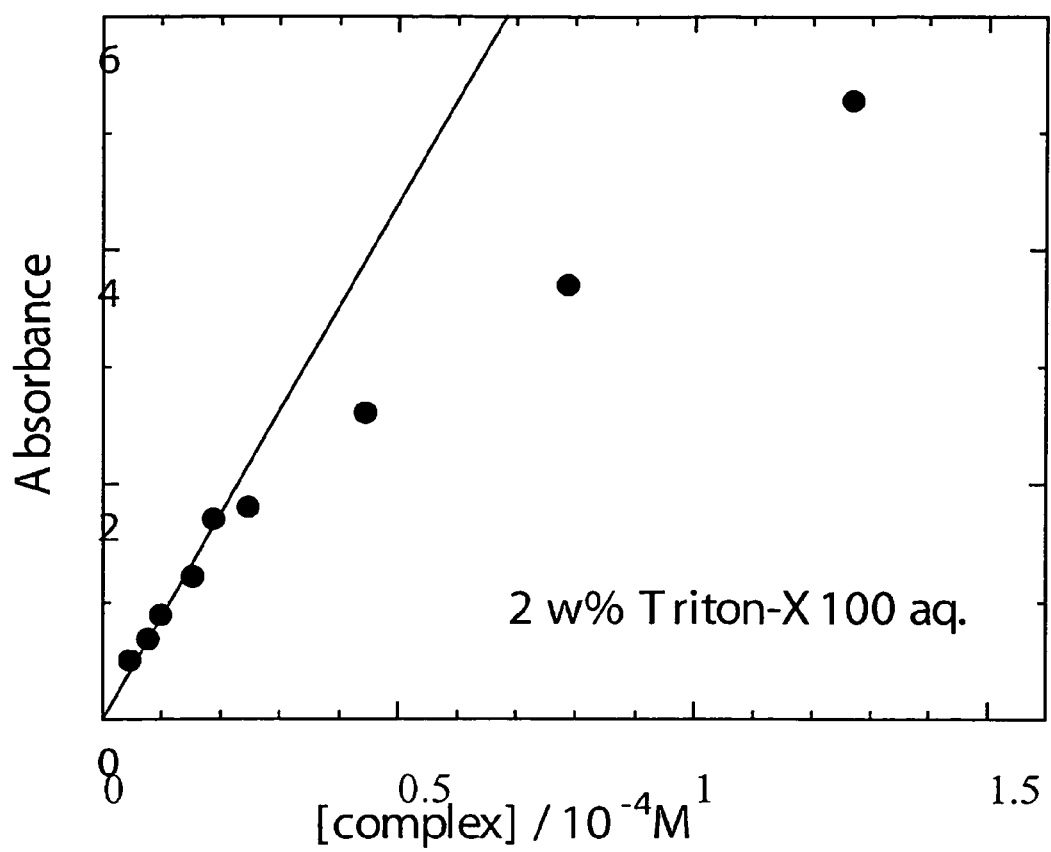
FIG. 9 is a graph indicative of the concentration dependence of the optical absorption spectra of Compound 2 in Table 1.

Although Compound 2 is soluble in pure water in a slight (0 to about $10^{-6}$ M), yet there is strong aggregation. In the presence of Triton-X100 (one commercially available surfactant sold under that trademark from Union Carbide Co., Ltd., however, the solubility of Compound 2 grows high. Moreover, above certain concentration of the surfactant, it remains dissolved in a disaggregated form (FIG. 8). With the concentration of the surfactant kept constant (2% (w/v)), effects of concentration of Compound 2 on optical intensity at a main absorption band at around 730 nm are shown in FIG. 9 with the ordinate indicating an absorbance at the main absorption band at around 730 nm (absorption maximum wavelength). Without aggregation, the dye exists in a monomer form, and the absorbance will increase in proportion to the concentration of the dye (Lambert-Beer law). FIG. 9 reveals that even in the presence of the surfactant at a concentration as low as 2%, the dye remains disaggregated up to a relatively high concentration ($2 \times 10^{-5}$ M).

Although Compound 1 is soluble in pure water in a slight, amount (0 to about $10^{-6}$ M) as is the case for Compound 2, yet there is very strong aggregation. As the addition of Triton-X100 makes much more improvements (>50 times) in solubility so that Compound 1 remains mostly aggregated even in a 20% (w/v) aqueous solution of Triton-X100 although disaggregation takes place only partly.

Compound 3 is not dissolved whatsoever in pure water or a high-concentration (30% (w/v)) of an aqueous solution of Triton-X100.

The water solubility of Compounds 1, 2 and 3 is greatly improved by the addition of alcohol to them.

Figure 7:
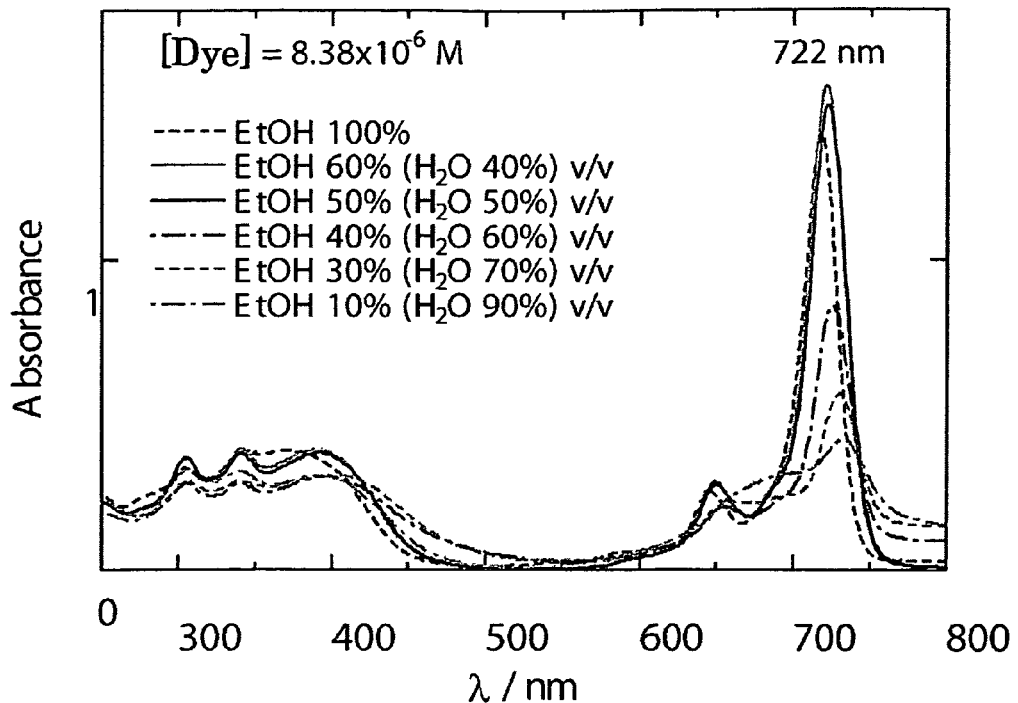
FIG. 7 is a graph indicative of the optical absorption spectra (mixed water/ethanol solvent) of Compound 2 in Table 1.

Optical absorption spectra of Compound 2 in an aqueous solution is affected by the addition of ethanol to it. FIG. 7 is indicative of effects of ethanol on the optical absorption spectra of Compound 2 with the concentration of the dye in each solution kept constant. As described above, the solubility of Compound 2 in pure water is low; however, in the presence of 10% (v/v) of ethanol, the solubility is much more improved (>100 times) although Compound 2 is considered to be in a substantially aggregated form. However, the higher the ethanol concentration, the higher the ratio of disaggregated species, and at 30% (v/v) concentration, a peak ascribable to disaggregated species is clearly observed. In the presence of 50% ethanol, contribution of aggregated species is negligible, and essentially the same spectra to those in pure ethanol are observed. Why the absorption peak position varies with solvent compositions could be due to solvent effects.

Similar tendencies are seen for Compounds 1 and 3, too.

TABLE 1

Variations of the peripheral substituents
($R^1$, $R^2$ in FIG. 2) in the example

| Compounds | Substituents $R^{1,3,5,7}$ | Substituents $R^{2,4,6,8}$ |
|---|---|---|
| 1 | H | H |
| 2 | H *1 | —$C(CH_3)_3$ *1 |
| 3 | H *1 | —$O(CH_2)_3CH_3$ *1 |

*1 Actually, either one of ($R^1$, $R^2$) (or ($R^3$, $R^4$), ($R^5$, $R^6$), ($R^7$, $R^8$)) was substituted, resulting in a mixture of 4 regional isomers.

APPLICABILITY TO THE INDUSTRY

Water-soluble phthalocyanine dyes could find many applications to printing in combination with inkjet techniques, homogeneous catalysts for hydrogen evolution in fuel cells and for purification of industrial waste (photo-decomposition of harmful organic matters), and photosensitizers in photo-dynamic treatment of cancers (PDT).

What is claimed is:

1. A water-soluble phthalocyanine dye, characterized by having a sulfuric acid group or groups as an axial ligand or ligands of an antimony/phthalocyanine complex.

* * * * *